United States Patent [19]

Asselineau et al.

[11] Patent Number: 4,474,647

[45] Date of Patent: Oct. 2, 1984

[54] PROCESS FOR PURIFYING A $C_4$ AND/OR $C_5$ HYDROCARBON CUT CONTAINING WATER AND DIMETHYL ETHER AS IMPURITIES

[75] Inventors: Lionel Asselineau, Paris; Jacques Leonard, Montigny; Jean Chodorge, Antony; Jean Gaillard, Lyons, all of France

[73] Assignee: Institut Francais du Petrole, Rueil-Malmaison, France

[21] Appl. No.: 371,341

[22] Filed: Apr. 23, 1982

[30] Foreign Application Priority Data

Apr. 24, 1981 [FR] France ................. 81 08391

[51] Int. Cl.$^3$ ............................................. C07C 7/04
[52] U.S. Cl. ..................................... 203/49; 203/14; 203/94; 203/98; 208/356; 585/518; 585/809
[58] Field of Search .................. 203/49.14, 98, 91, 94; 585/809, 800, 18, 264, 502, 510, 518, 519; 568/697, 699; 208/185, 187, 347, 356, 362

[56] References Cited

U.S. PATENT DOCUMENTS

| | | | |
|---|---|---|---|
| 2,368,497 | 1/1945 | Shipley et al. | 203/14 |
| 2,485,329 | 10/1949 | Steele et al. | 568/699 |
| 2,994,644 | 8/1961 | Clay | 203/98 |
| 3,225,113 | 12/1965 | McNulty et al. | 568/699 |
| 3,296,314 | 11/1974 | Statman et al. | 568/699 |
| 3,847,756 | 8/1980 | Chase et al. | 585/518 |
| 4,218,569 | 11/1981 | Mikitenko et al. | 203/70 |
| 4,299,999 | 11/1981 | Mikitenko et al. | 568/699 |

*Primary Examiner*—Wilbur Bascomb
*Attorney, Agent, or Firm*—Millen & White

[57] ABSTRACT

A $C_4$ and/or $C_5$ olefinic hydrocarbon cut, containing dimethyl ether and water as impurities, in a relative proportion of dimethyl ether to water of at most 5:1, is purified in a distillation zone where it is introduced at an intermediate level, distant from the top or from the bottom thereof by at least 3 theoretical plates, optionally with a stripping gas, and separated into a overhead fraction comprising an aqueous liquid phase and a hydrocarbon liquid phase at least partially recycled as reflux to the upper part of the distillation zone, and a bottom fraction formed of the purified $C_4$ and/or $C_5$ olefinic cut.

17 Claims, 1 Drawing Figure

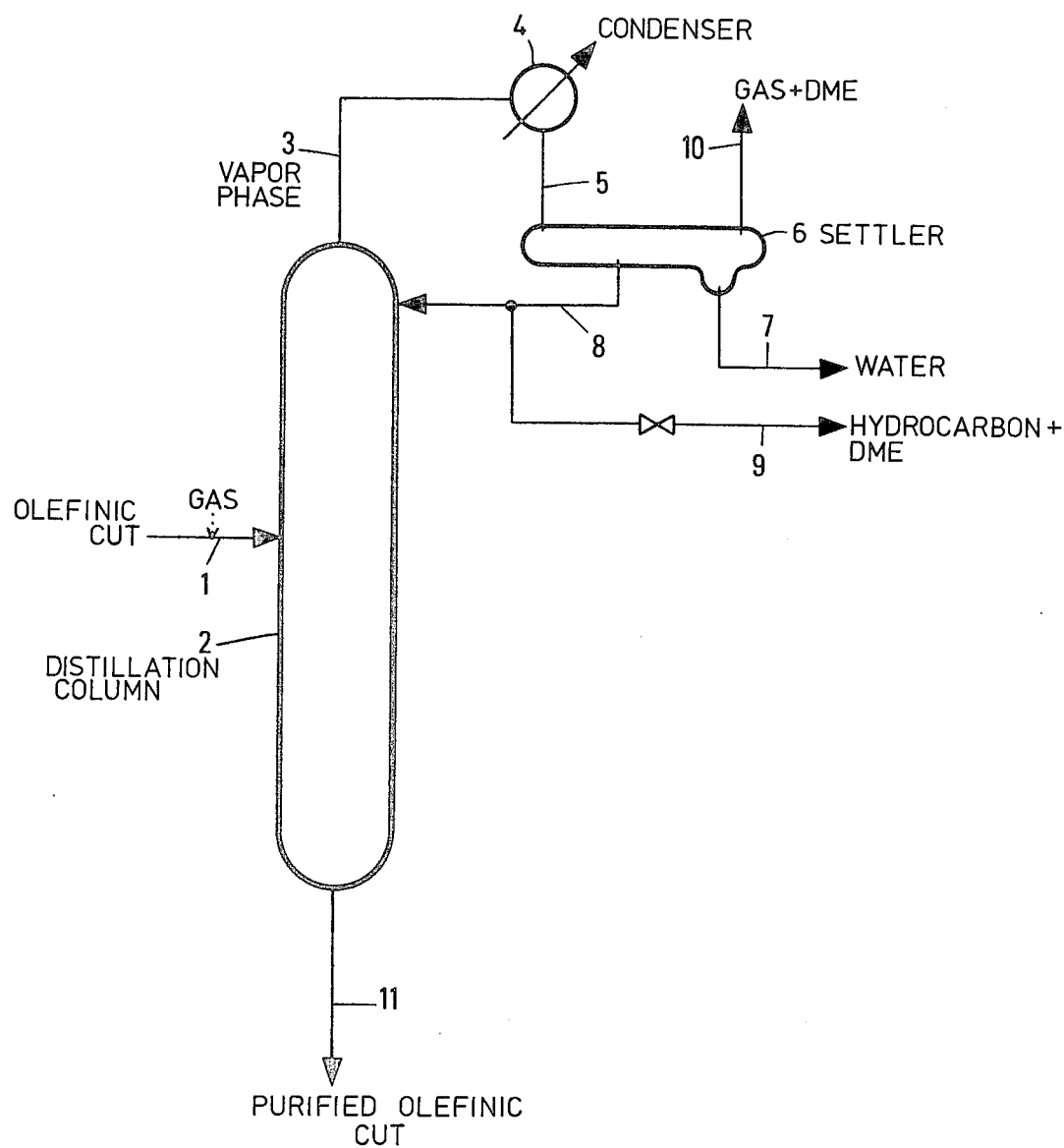

ately from the one or more formed mixed ether(s) did not give satisfactory results in oligomerization. As a matter of fact, the following drawback is observed: destruction of the metal organic compounds such as hydrocarbyl aluminum halides and, consequently, blocking of the olefin oligomerization reaction.

PROCESS FOR PURIFYING A C$_4$ AND/OR C$_5$ HYDROCARBON CUT CONTAINING WATER AND DIMETHYL ETHER AS IMPURITIES

BACKGROUND OF THE INVENTION

The invention concerns the purification of C$_4$ and/or C$_5$ hydrocarbon cuts containing, as impurities, water and dimethyl ether. It concerns more particularly the purification of C$_4$ and/or C$_5$ olefinic cuts, previously freed of at least a portion of the isobutene and/or isopentene thereof by reaction with methanol.

By isopentene, is meant mainly 2-methyl-1-butene and 2-methyl-2-butene.

It is already known to manufacture methyl tert-butyl ether (MTBE) and/or tert-amyl methyl ether (TAME) by reaction of methanol with isobutene and/or iospentene contained in an olefinic C$_4$ and/or C$_5$ hydrocarbon cut optionally containing other hydrocarbons. The isobutene and isopentene selectively react, whereas the other monoolefins remain practically unchanged. After separation of the methyl tert-butyl ether (MTBE) and/or tert-amyl methyl ether (TAME), the residual olefinic cut may be used as a charge in an oligomerization, particularly a dimerization, co-dimerization and/or trimerization process, as for example the so-called "Dimersol" process.

In this known oligomerization process, the olefin charge is contacted with a catalyst formed from a nickel compound, for example a nickel carboxylate, and a hydrocarbyl aluminum halide.

It has been observed that the olefinic cuts freed of isobutene and/or isopentene by reaction with methanol and separated from the one or more formed mixed ether(s) did not give satisfactory results in oligomerization. As a matter of fact, the following drawback is observed: destruction of the metal organic compounds such as hydrocarbyl aluminum halides and, consequently, blocking of the olefin oligomerization reaction.

Systematic experimentation has shown that these drawbacks are limited or even may disappear when the water and dimethyl ether content of the olefinic cut is reduced, dimethyl ether and water being by-products of the above-mentioned reaction of manufacture of MTBE and/or TAME.

It is particularly advantageous to reduce this content below 10 ppm by weight for water and below 50 ppm by weight for dimethyl ether.

Unfortunately, this removal is particularly difficult to achieve in an efficient manner without resulting in a substantial loss of olefins.

The invention provides for a process whereby the purification of said cuts may be achieved under particularly advantageous conditions.

SUMMARY OF THE INVENTION

The separation according to the present process requires control of the proportions of dimethyl ether (DME) and water in the olefinic charge so as to obtain a critical ratio by weight DME/water lower than or equal to 5:1, for example from 0.03:1 to 5:1. When this ratio is not controlled, particularly when it is higher than 5:1, a non-negligible proportion of water remains in the olefinic cut after purification, and this is unacceptable.

The olefinic charge to be purified, which contains at least one mono-olefinic hydrocarbon, dimethyl ether, water and, optionally, one or more saturated hydrocarbons, is first introduced into a distillation zone, at an intermediate level thereof; the overhead effluent is condensed and separated into two liquid phases, an aqueous phase which is withdrawn and a hydrocarbon phase at least a portion of which is fed back as reflux to the distillation zone. At the bottom of the distillation zone, the purified C$_4$ and/or C$_5$ cut is recovered.

BRIEF DESCRIPTION OF THE DRAWING

FIG. 1 is a schematic flow diagram of the process of the invention

DETAILED DISCUSSION

The removal of dimethyl ether from the distillate may be effected according to two modes of operation which are not mutually exclusive and may accordingly be used simultaneously.

According to a first mode of operation, a portion of the hydrocarbon liquid phase, carrying along therewith the DME, is removed, another portion of said phase forming the reflux.

According to another mode of operation, a stripping gas is present in the distillation charge or added thereto; in this case, at least a portion of the DME is carried along in the gas phase by said stripping gas. The latter preferably consists of a known non-oxidant gas, for example hydrogen, nitrogen, argon, methane or ethane.

The distillation charge is introduced at an intermediate point of the distillation zone, i.e. at a point separated from the bottom and from the top of the column by, for example, at least 3 plates. Preferably, the introduction point is located at a distance from 15% to 40% of the total effective height of the column, measured from the top, downwardly.

The reflux, expressed as hydrocarbon phase hourly volume fed back to the distillation zone, is advantageously from 0.25 to 0.8 times and preferably from 0.4 to 0.7 times the hourly volume of hydrocarbon charge of the column.

The temperature depends on the distillation pressure, this pressure being advantageously between 3 and 15 bars.

The accompanying figure illustrates the present invention without limiting the scope thereof. The C$_4$ cut to be purified is fed through line 1 to the distillation column 2.

From the top, an overhead vapor phase is withdrawn through line 3; this vapor phase passes through the condenser 4, cooled by an external fluid. The condensate passes through line 5 to the settler 6. Two phases separate. Water is discharged from line 7 and the hydrocarbon phase is fed back, partially or entirely, to the column, through line 8, as reflux. This reflux is introduced, at least partly, at the top of the column. Line 9 makes it possible, if so desired, to withdraw a portion of the hydrocarbon phase carrying the DME along therewith, particularly when no stripping gas is present in the distillation charge; when such a gas is introduced, e.g. through line 1, it is discharged through line 10, carrying therewith a portion or the totality of the DME. From the bottom, the purified C$_4$ cut is withdrawn through line 11.

The invention is not limited to the purification of hydrocarbon cuts issued from a reactor for the manufacture of MTBE or TAME; it applies more generally to the purification of C$_4$ and/or C$_5$ hydrocarbon cuts from any origin, containing water and dimethyl ether.

EXAMPLE

An olefinic C$_4$ cut containing 800 ppm by weight of water and 500 ppm by weight DME is introduced into a distillation column at a point located at 30% of the total effective height of the column, counted downwardly from the top.

The reflux rate, expressed as hourly volume of hydrocarbon phase fed as reflux, is about 0.5 times the hourly volume of the hydrocarbon charge to the column.

The pressure is about 6 bars.

The C$_4$ cut is recovered at the bottom of the column. By analysis of this cut, it has been determined that the removal rate was 99.5% for water and 98% for DME.

What is claimed is:

1. A process for purifying a C$_4$ and/or C$_5$ olefinic hydrocarbon cut, containing both dimethyl ether (DME) and water as impurities therein, which comprises the steps of: adjusting and maintaining the DME/water weight ratio in said cut at from 0.03.:1 to 5:1, introducing said cut, having said DME/water weight ratio, into a distillation zone, at an intermediate level thereof, fractionating said cut, and separately recovering a gaseous overhead stream, and a liquid bottom stream comprising a purified C$_4$ and/or C$_5$ olefinic hydrocarbon product cut; condensing said gaseous overhead stream, and separately recovering an aqueous liquid phase and a liquid hydrocarbon phase; and discharging said aqueous liquid phase, and returning at least a portion of said liquid hydrocarbon phase to the upper portion of said distillation zone as reflux.

2. A process according to claim 1, wherein the olefinic cut is introduced at a point located at a distance of at least 3 theoretical plates from the top and from the bottom of the distillation zone.

3. A process according to claim 1 wherein the olefinic cut is introduced into the distillation zone at a point located at a distance of from 15 to 40% of the effective height of the distillation zone, measured downwardly from the top of said zone.

4. A process according to claim 1, wherein the reflux ratio, expressed as the hourly volume of said reflux to the hourly volume of the olefinic cut introduced into said distillation zone, is from 0.25 to 0.8.

5. A process according to claim 4, wherein said reflux ratio is from 0.4 to 0.7.

6. A process according to claim 1, wherein the pressure in said distillation zone is 3–15 bars.

7. A process according to claim 1, wherein said purified olefinic product cut contains less than 10 ppm of water.

8. A process according to claim 1, wherein said purified olefinic product cut contains less than 50 ppm of DME.

9. A process for purifying a C$_4$ and/or C$_5$ olefinic hydrocarbon cut, containing both dimethyl ether (DME) and water as impurities therein, which comprises the steps of: adjusting and maintaining the DME/water weight ratio in said cut at from 0.03:1 to 5:1, introducing said cut, having said DME/water ratio, into a distillation zone, at an intermediate level thereof, concomitantly introducing a stripping gas into said distillation zone, fractionating said cut, and separately recovering a gaseous overhead stream, and a liquid bottom stream comprising a purified C$_4$ and/or C$_5$ olefinic hydrocarbon product cut; cooling and partially condensing said gaseous overhead stream, and separately recovering a stripping gas stream containing DME, an aqueous liquid phase, and a liquid hydrocarbon phase; and discharging said stripping gas stream and said aqueous liquid phase, and returning at least a portion of said liquid hydrocarbon phase to the upper portion of said distillation zone as reflux.

10. A process according to claim 9, wherein the olefinic cut is introduced at a point located at a distance of at least 3 theoretical plates from the top and from the bottom of the distillation zone.

11. A process according to claim 9, wherein the olefinic cut is introduced into the distillation zone at a point located at a distance of from 15 to 40% of the effective height of the distillation zone, measured downwardly from the top of said zone.

12. A process according to claim 9, wherein the reflux ratio, expressed as the hourly volume of said reflux to the hourly volume of the olefinic cut introduced into said distillation zone, is from 0.25 to 0.8.

13. A process according to claim 14, wherein said reflux ratio is from 0.4 to 0.7.

14. A process according to claim 9, wherein the pressure in said distillation zone is 3–15 bars.

15. A process according to claim 9, wherein said purified olefinic product cut contains less than 10 ppm of water.

16. A process according to claim 9, wherein said purified olefinic product cut contains less than 50 ppm of DME.

17. A process according to claim 9, wherein said stripping gas is hydrogen, nitrogen, argon, methane or ethane.

* * * * *